United States Patent [19]

Ishida et al.

[11] 4,442,006
[45] Apr. 10, 1984

[54] ANAEROBIC DIGESTION PROCESS

[75] Inventors: Masahiko Ishida; Ryooichi Haga; Yoji Odawara, all of Hitachi, Japan

[73] Assignee: The Agency of Industrial Science and Technology, Tokyo, Japan

[21] Appl. No.: 327,227

[22] Filed: Dec. 3, 1981

Related U.S. Application Data

[63] Continuation of Ser. No. 140,677, Apr. 15, 1980, abandoned.

[30] Foreign Application Priority Data

Apr. 24, 1979 [JP] Japan .................................. 54-49751

[51] Int. Cl.$^3$ .............................................. C02F 3/28
[52] U.S. Cl. .................................... 210/613; 210/614
[58] Field of Search ............... 210/603, 605, 610, 613, 210/614, 631

[56] References Cited

U.S. PATENT DOCUMENTS

| | | | |
|---|---|---|---|
| 2,029,702 | 2/1936 | Buswell et al. | 210/603 |
| 3,259,566 | 7/1966 | Torpey | 210/603 |
| 4,040,953 | 8/1977 | Ort | 210/603 |
| 4,067,801 | 1/1978 | Ishida et al. | 210/603 |
| 4,318,993 | 3/1982 | Ghosh et al. | 210/603 X |

FOREIGN PATENT DOCUMENTS 54-136747 10/1979 Japan .................................. 210/603

Primary Examiner—Thomas G. Wyse
Attorney, Agent, or Firm—Birch, Stewart, Kolasch & Birch

[57] ABSTRACT

First, the organic waste slurry of sewage sludge and/or kitchen garbage is stored in a stable condition after effecting partially thereto a liquefaction treatment in advance by adding liquefying bacteria, and next this slurry is effectively digested anaerobically by way of a liquefaction/gasification-mixed step or a liquefaction/gasification separated step.

18 Claims, 4 Drawing Figures

ANAEROBIC DIGESTION PROCESS

This application is a continuation of copending application Ser. No. 140,677, filed on Apr. 15, 1980, abandoned.

BACKGROUND OF THE INVENTION

1. Field of the Invention

The present invention relates to an anaerobic digestion process for organic wastes, particularly the anaerobic digest process which effectively copes with the widely fluctuating quantitative load of an organic waste slurry.

2. Description of the Prior Art

The anaerobic digestion process is known as one of the treating processes of such thick organic wastes as sewage treatment sludge, human/animal feces and alcohol distillery waste. This process transforms organic wastes into volatile fatty acids and then into methane, by the activities of the liquefying bacteria of the facultative anaerobic bacteria group, namely acidifying bacteria, and the gasifying bacteria of the obligatory anaerobic bacteria group. Furthermore, this process has characteristic features in that it has little possibility of spreading a secondary pollution and can be used as a driving power source of the facilities which treat the recovered methane gas. For these reasons, there is a move in recent years to employ it for treating not only water treatment sludge or human/animal feces but also wastes from various food processing industries.

In this concern, however, in many cases the volume of wastes discharged naturally varies widely during a day, a week or a year, so that in anticipation of such a wide fluctuation in the volume of wastes discharged, and in consideration of the varying volume of feed and impact of the scum generated, in most cases the digesters presently in operation are designed with a dimension for applying a safety coefficient around a double of the standard treatment volume of a digester. As the reaction of the anaerobic digestion process is slow, however, it is remarkably vulnerable to the impact of a sudden fluctuation in the feed load. In practice, in many cases the feed wastes are charged into the digester disregarding the above vulnerability, so that a significant number of digesters in this country are said to have been at a state of unsatisfactory operation. Therefore, in order to operate a digester while stably maintaining a high activity, the storing of feed organic wastes becomes imperative by all means. Conventionally, however, digesting the feed wastes after storing has been seen only in a few limited cases. In other words, a simple open-air storage permits generation of stink on account of decomposition and incurs a loss of chemical energy contained in the feedstock due to a biochemical oxidation by aerobic microorganism, which eventually invites a reduction in the methane recovery rate. These facts so far have discouraged storing the feed slurry. Also in a case of simple air-tight anaerobic storage, a partial gasification takes place in the course of storing whereby generating a gas of a lower methane concentration, which reduces the usable volume of recovered gas or results in a considerable amount of scum generation in the course of the subsequent digestion process.

SUMMARY OF THE INVENTION

The purpose of the present invention is to provide an anaerobic digestion process of organic wastes which is capable of effecting an effective anaerobic digestion by storing under a qualitatively stable condition the feed organic wastes which are susceptible to decomposition and degeneration that are disadvantageous to anaerobic digestion.

The anaerobic digestion process of organic waste under the present invention is characterized in subjecting the organic waste slurry to a gasification treatment by applying thereto liquefaction bacteria and gasification bacteria of the obligatory anaerobic bacteria group capable of producing methane, after effecting a partial liquefaction treatment in advance while stirring the feed organic waste slurry under the presence of the liquefying bacteria of facultative bacteria capable of producing volatile fatty acids but without any pH adjustment.

By the partial liquefaction step in the first part of this anaerobic digestion process under the present invention, the storage life of the slurry is outstandingly improved thereby permitting storage without any significant degeneration, at least a week or so, and facilitating the upgrading of the purity of the methane gas which is generated in the gasification step in the latter part of the process under review.

In a desirable embodiment of the process under the present invention, the amount of the organic wastes which is partially liquefied at the earlier part of the process can be varied within the range of 20–100% (vol./vol.) in dimensions of the partial liquefaction tank.

In another desirable embodiment, the feed organic waste slurry is subjected to a liquefaction treatment until its pH becomes 2–4.5, in the course of a partial liquefaction treatment of the feed slurry.

For the gasification step in the latter part of the process under the present invention, where liquefying bacteria and gasification bacteria are employed, either the separation method which performs a liquefaction step and gasification step successively and independently, or the method which performs these two steps simultaneously in parallel within the same digester can be employed.

The partial liquefaction step in the first half of the process under the present invention is performed within the temperature range lower than, or identical to, or most close to that of the liquefaction step in the latter half of the process (in case of a parallel liquefaction/gasification, the temperature range of that liquefaction/gasification step).

Under the process of the present invention, in the case of one embodiment, where the partial liquefaction step in the first half of the process is carried out within the temperature range identical to or most close to that of the liquefaction step or the liquefaction/gasification step in the latter half of the process, a part of the slurry treated in the latter half of the process is recycled back to the first half of the process. Further summing up the characteristics of the process under the present invention, the first characteristic point of the present invention is its storing of the feed slurry prior to the main fermentation, while partially liquefying and fermenting the stored slurry. If any attempt be made to store the slurry under a simple air-tight condition without the presence of liquefying bacteria, partial gasifying fermentation (generation of methane) and lactate fermentation take place and it generates methane gas with concentration lower than 20–30% of methane. This gas is not only usable as the driving power source of the digestion treatment facilities, but also it has to be subjected to another treatment as an additional waste. Also, the amount of energy recovered from the feed organic wastes is to be correspondingly reduced.

When organic material is digested by means of liquefying bacteria and gasifying bacteria, it is known that it normally generates methane and carbon dioxide in equal volume. By the process under the present invention, however, it facilitates increasing the concentration of the methane contained in the gas recovered at the main fermentation step in the latter half of the process, on account of a part of the carbon dioxide being generated at the partial liquefaction step in the earlier half of the process. In case the feedstock is stored under a simple air-tight condition with no manipulation, normally a methane fermentation takes place in part as mentioned above. Each if it does not, sometimes lactate fermenting bacteria become dominant, and organic ingredients are transformed into lactic acid without generating carbon dioxide. Thus generated lactic acid does not suit the volatile fatty acid fermentive liquefying bacteria, and it is decomposed into carbon dioxide and methane by gasifying bacteria and other bacteria that decompose lactic acid at the gasification step. So that, in case the latter half of the process is separated into a liquefaction step and gasification step, the purity of the methane gas which is obtained from the gasification step in the latter half of the process is degraded.

The second characteristic point of the present invention is its capability of digesting and treating the feed organic waste slurry, after its partial liquefaction, either by a separation system of liquefaction and gasification or by a simultaneous/parallel system of liquefaction and gasification. The former system is recently attracting much attention, and is said, as compared with the conventional latter system, to be the method which permits shortening the number of days required for treatment and makes it possible to obtain a gas with a higher methane concentration.

The third, but not the least, characteristic point of the present invention is that the partial liquefaction step in the first half of the process can be performed within the temperature range identical to, or close to, that of the main fermentation step in the latter half, and that a part of the slurry treated at the liquefaction step or the liquefaction/gasification simultaneous treatment step can be recycled back to the liquefaction step in the first half of the process for further treatment. This process makes it possible to improve the treatment efficiency of the partial liquefaction step.

In the following, further detailed explanatory description of the present invention is made by quoting examples and referring to attached drawing, but all of them are no more than exemplifications and evidently various sorts of improvements and modification are possible without varying from the framework of the present invention.

DESCRIPTION OF THE PREFERRED EMBODIMENTS

Figure 1:
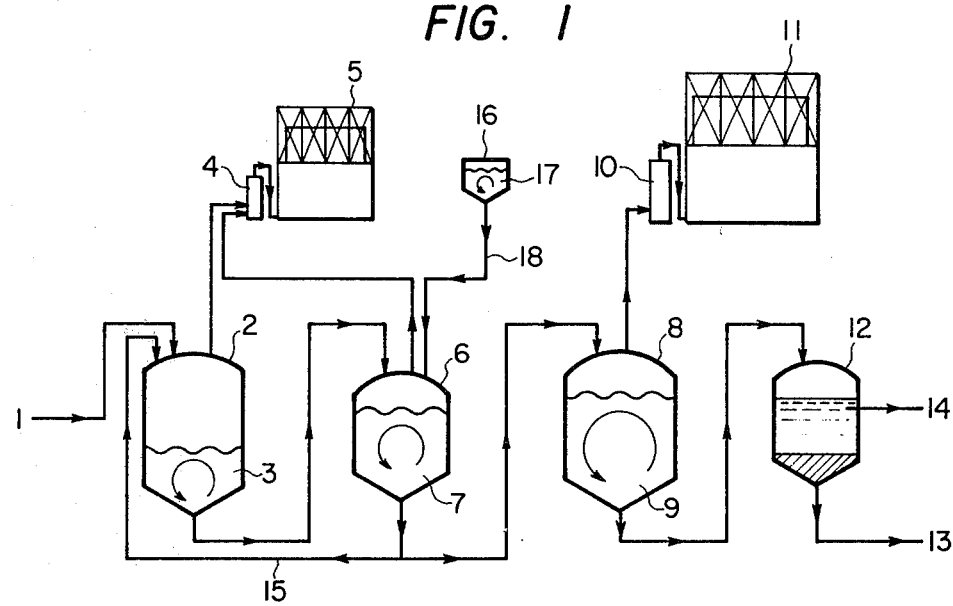
FIG. 1 and FIG. 2 respectively represent process charts of one example of the present invention.
Figure 2:
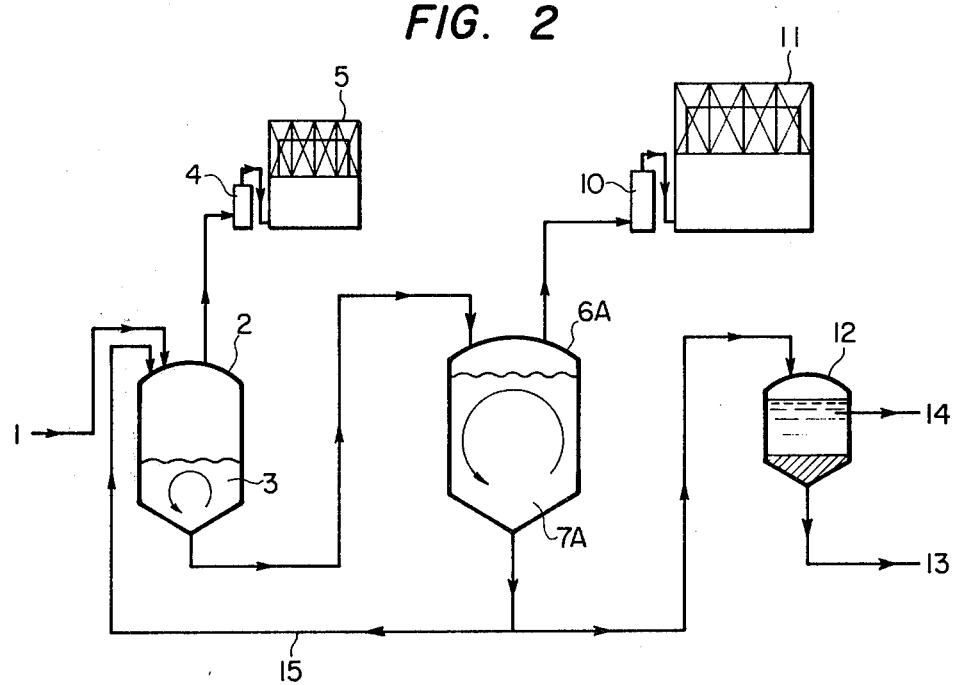

FIG. 1 indicates the system performing separately the liquefaction step and the gasification step of the main fermentation in the latter half of the process, and FIG. 2 shows the system which carries out the liquefaction step and the gasification step simultaneously in parallel.

As for the organic wastes which are subjected to the process under the present invention, there are sewage sludge, thickened waste water and wastes discharged from food processing industries, kitchen garbage and human/animal feces. First, the organic waste in a slurry form (1) is charged into the partial liquefaction treatment tank (2) at the rate equal to discharge. The feed slurry (1) could be slurry being supplied from the discharging source without any pre-treatment, or one which is pre-treated in advance so as to make it easy to ferment. As for examples of pre-treatment, there are heat treatment of the slurry under an alkali or acidic condition, removal of such foreign matters as pieces of metal, plastics, dirt and sand, pulverization of solids contained in the slurry in order to induce subsequent steps easy and perparation of slurry by mixing waste water or water with the solid wastes. Particularly, the pre-treatment of sewage sludge or kitchen garbage by heating up to 50° C. or more with a pH above 8 is most useful for improving the transportability of the slurry and encouraging the subsequent main fermentation.

The partial liquefaction treatment tank (2) has a capacity in excess of the daily average discharging volume with an air-tight structure, and is designed to facilitate effective stirring of the contained slurry within the range of 20–100% (volume/volume) of its effective capacity.

No specific stirring method is required, and any method that fits the concentration of solids and the viscosity of the slurry, such as mechanical stirring or gas injection stirring, can be employed. To the feed slurry charge into the partial liquefaction treatment tank (1), as the seeds for liquefaction, the partially liquefied slurry that is remaining in the tank, or, in case the partial liquefaction is performed at the temperature identical or approximate to that of the subsequent liquefaction or liquefaction/gasification step, the slurry recycled back from the liquefaction tank (6) or the liquefaction/gasification tank (6A) through the recycling pipe (15), is applied. The suitable volume of the seeds is 5% or more (volume/volume) of the feed slurry charged in. As for liquefaction bacteria, those which decompose starch, protein and fats into volatile fatty acids, for instance, clostridium, bacillus, escherichia or staphylococcus, can be used independently or by mixing two or more together as a bacteria group. No adjustment of pH is made, and the range of temperature is 10°–45° C., preferably 10° to 30° C., corresponding to the so-called mesothermophilic range. The temperature, however, can be either adjusted to a certain level or without adjustment.

As stated above, the liquefaction fermentation takes place through the feed slurry contact with the liquefaction bacteria under an anaerobic condition, and the liquefaction fermentation automatically ceases to continue itself at the stage where the pH is lowered down to 4.5–2.0 as the volatile fatty acid is increasingly generated. At this stage, low-molecularization and fatty acid generation make partial progress, and the concentration of the volatile fatty acid within the slurry reaches to 4,000–15,000 ppm. If any adjustment of pH be made by injecting alkali, the fermentation would progress further and would reach its critical point. If the above partial liquefaction treatment be exercised, the organic waste slurry (3) could be stored after terminating its fermentation under an anaerobic condition for at least 1–2 weeks with little gas generation and under a stabilized condition.

On the other hand, the gas generated in the course of the partial liquefaction treatment is stored in the carbon dioxide storage tank (5) after its trace content of hydrogen sulfide is removed at the desulfurization tower (4). The ingredients of the generated gas are a small amount of hydrogen, nitrogen and hydrogen sulfide in addition to its main ingredient of carbon dioxide, but no methane. For guidance, this partial liquefaction treatment can be exercised either batchwise or continuously.

As the next step, the above partially liquefied slurry (3) is charged into either the liquefaction tank (6) or the liquefaction/gasification tank (6A), as the case may be. First, explanation is made on FIG. 1, Process Chart, wherein the slurry (3) is charged into the liquefaction tank (6).

At the liquefaction tank (6), the partially liquefied slurry is repeatedly subjected to liquefaction treatment by means of stirring under the presence of liquefaction bacteria and an anaerobic condition with its temperature and pH automatically adjusted to a designated level. So as to set the pH at 5–6, lime emulsion (16) from the lime storage tank (17) is automatically supplied to the liquefaction tank (6) through the lime supply pipe (18). At this liquefaction step, the low molecularization and conversion to volatile fatty acids make advance, following those at the preceding partial liquefaction treatment, and it reaches the critical level of liquefaction fermentation. For the liquefaction bacteria at this step, the same species of bacteria which are used at the aforementioned partial liquefaction treatment are employed. In case, however, fermentation is performed in the so-called high temperature range of 45°–75° C., a high-temperature bacterium, out of the aforementioned species of bacterium, has to be used, so that it differs from the low/medium-temperature bacteria employed at the preceding partial liquefaction step. In this case, the liquefied slurry (7) is not recycled back to the partial liquefaction tank. The gas generated at the liquefaction tank (6) does not contain any methane, similar to that from the partial liquefaction treatment, and mainly consists of carbon dioxide, and is stored in the carbon dioxide storage tank (5) after being channelled through the desulfurization tower (4).

Next, the liquefied slurry is transferred into the gasification tank (8), where the gas enriched with methane is generated by having the slurry contact the gasification bacteria while the slurry is kept stirred under an anaerobic condition and a given temperature. The temperature range applied is 10°–75° C. As for the methods of keeping the slurry heated and stirred, those which are employed at the aforementioned liquefaction step sufficiently attain the purpose. Normally, without any intended adjustment of pH, the pH of the slurry spontaneously settles down to the range of 7–8 which suits gasification fermentation. But, in case the pH exceeds 8, it may be necessary to add some mineral acid or organic acid. As for the gasifying bacterium, such gasifying bacteria conventionally in use as those belonging to methanosarcina, methanococcus or methanobacterium are fully applicable.

In terms of volumetric percentage, the generated gas contains, 60–90% of methane as its principal ingredient plus trace amounts of nitrogen and hydrogen sulfide. The methane gas generated at this gasification step is passed through the desulfurization tower (10) before it is stored in the methane storage tank (11).

In the example as per FIG. 2 where the partially liquefied slurry (3) is charged into the liquefaction/gasification tank (6A), the partially liquefied slurry is stirred in the liquefaction/gasification tank (6A) under an anaerobic condition with a simultaneous presence of the liquefying bacteria and the gasifying bacteria, the mixed gas thus generated is lower in its concentration of methane than the gas generated from the gasification tank (8) cited in the example of FIG. 1. The mixed gas is the mixture of methane and carbon monoxide. This gas is stored in the methane storage tank (11) similar to the example shown in FIG. 1. In this case as well, similar to the case as per FIG. 1, the liquefied/gasified slurry (7A) is not recycled back to the partial liquefaction tank (2), when thermophilic bacteria are used as the liquefying bacteria, at the liquefaction/gasification tank (6A).

The gasified slurry (9) (refer to FIG. 1) and the liquefied/gasified slurry (7A) (refer to FIG. 2), both after digestion, are sent to the solid/liquid separation tank (12) and are separated into the digested sludge (13) and the treated water (14).

In the following further explanation is made by citing practical examples of the process under the present invention.

EXAMPLE 1

20 kg of sewage sludge (solid concentration 24%, organic concentration in the solids 65%) derived from city sewage treatment was charged into a 30 l digester made of acrylic plastics with a stirrer and a warm water jack installed. Next, 1 kg of digested slurry which had been prepared by acclimating the sewage sludge taken from the identical batch for a certain extended period of time under a temperature of 30° C. was charged into the aforementioned digester, and a partial liquefaction treatment was performed for 7 days while the feed in the digester was kept stirred at 40 rpm (peripheral speed 30 m/min) under an anaerobic condition. This is designated as Example 1.

On the other hand, as a comparable example, the following 4 kinds of pre-treatments were exercised, prior to the main digestion step:

As Comparative Example 1; the pre-treatment was made with the lid of the digester not completely closed airtight whereby permitting the air to get in contact with the surface of the slurry, but otherwise the rest remained exactly same as Example 1.

As Comparative Example 2; the pre-treatment was made with all conditions kept unchanged from Example 1, but without the digestive sludge added.

As Comparative Example 3; the pre-treatment was exercised with all conditions kept unchanged from Example 1, but without stirring and the digestive sludge added.

As Comparative Example 4; in lieu of the pre-treatment as Example 1, the feed slurry was stored in the refrigerator at 2°–5° C.

The changes appeared in the total gas product, the total methane product and the pH respectively of Example 1 and Comparative Example 2 are shown in Table 1 attached.

TABLE 1

| | pH of Slurry | | | | Total Gas Product (Nl/kg · VS) | | | Total Methane Product (Nl/kg · VS) | | |
|---|---|---|---|---|---|---|---|---|---|---|
| Number of Day | 0 | 2 | 4 | 7 | 2 | 4 | 7 | 2 | 4 | 7 |
| Example 1 | 6.7 | 4.5 | 4.4 | 4.1 | 47.5 | 52.0 | 53.3 | 0 | 0 | 0 |
| Comparative Example 2 | 6.7 | 6.2 | 6.8 | 6.9 | 2.0 | 11.1 | 52.0 | 0.3 | 4.6 | 21.5 |

Note:
Nl/kg · VS-The number of liter per each 1 kg of the organic solids in the slurry under a standard condition.

As it is clearly known from Table 1, when the process under the present invention is employed as per Example 1, the partial liquefaction is completed within 2 days, and it can be stored at least for 7 days, without any subsequent gas generation and any change in quality. On the other hand, in the case of Comparative Example 2, it is known that some part of the methane gas is lost by the partial liquefaction treatment on account of a gasification fermentation which takes place in parallel with the liquefaction, as no liquefying bacterium is added.

The slurry pre-treated by the respective processes as per Example 1 and Comparative Example 1, 2, 3 and 4 was subjected to the treatment by the liquefaction/gasification-mixed step and the liquefaction/gasification-separated step respectively, and the respective results are shown in Table 2.

Either cases were carried out for a continuous treatment for 20 days with a load of 0.33 kg.slurry/day. In the case of the liquefaction/gasification-mixed step, a 4 l tank made of acrylic plastics with a stirrer and a warm water jacket was used as a digester, and the residential time of slurry was set at 12 days.

As regards the case of the liquefaction/gasification-separated step, the partially liquefied slurry was fed into a 1.5 l liquefaction treatment tank, with a stirrer, a warm water jacket and an automatic pH adjuster, at the rate of 0.5 kg slurry/day. The residential time was 3 days. Next, the thus liquefied slurry was transferred to a 4.5 l gasification treatment tank with a stirrer and a warm water jacket and the gasification treatment was made. The residential time was 9 days.

The pre-treated slurry by the process as per Example 1 was treated by the aforementioned two steps, and these two cases are designated as Examples 1-1 and 1-2 respectively, while the pre-treated slurries obtained respectively by the processes shown in Comparative Examples 1 through 4 were treated only by the former liquefaction/gasification-mixed step and these four cases are nominated as Comparative Examples 1-1, 2-1, 3-1 and 4-1 respectively.

TABLE 2

| | Average Gas* Product per Day (Nl/kg · VS) | Average Methane Product per Day (Nl/kg · VS) | Purity of Methane (Volume %) |
|---|---|---|---|
| Example 1-1 | 418.0 | 271.7 | 65 |
| Example 1-2 | 423.0 | 286.0 | 80** |
| Comparative Example 1-1 | 266.5 | 131.3 | 46 |
| Comparative Example 2-1 | 380.0 | 237.1 | 62 |
| Comparative Example 3-1 | —*** | — | — |
| Comparative Example 4-1 | 481.0 | 276.3 | 60 |

Note:
*This excludes the amount of gas product produced at the partial liquefaction step (pre-treatment), but only the gas produced at the main fermentation step is indicated.
**This indicates the methane concentration in the recovered gas from the gasification tank. No methane is detected in the gas recoverd from the liquefaction tank.
***Due to scum generation, the gas exit pipe was blocked and it was unable to operate.

As is clear from the aforementioned results, it will be made known that the same effect as to the recovered methane is available when the process under the present invention is employed as that of storing the slurry in a cold storage. Either of storing under an aerobic condition and a partial liquefaction treatment with no addition of liquefying bacteria have a drawback of reduction in the recovered amount of methane.

EXAMPLE 2

20 kg of kitchen garbage slurry (solid concentration 6%, organic concentration in the solids 91%) was prepared by crushing fresh restaurant garbage (discharge of the same day) by a disposer with some water added. Seeds for liquefaction were prepared by acclimating the slurry identical to the aforementioned one in a fermenter with the same specifications as the liquefaction treatment tank with a temperature set at 15° C. and pH at 5.8 for about a month. The kitchen slurry 20 kg and the seed slurry 1 kg were charged into a 30 l fermenter made of acrylic plastics with a stirrer and a warm water jacket attached, and were subjected to a partial liquefaction treatment for 7 days under anaerobic condition with a temperature set at 15° C. and a stirring velocity of 10 rpm (peripheral speed 7.5 m/min, but with pH unadjusted).

On the other hand, as a comparative example, the following 4 pre-treatment steps were performed prior to the main digestion. As Comparative Example 5, a pre-treatment was effected under the identical conditions as Example 2, with only exception of having it stored for 10 days with the lid not closed airtightly so as to permit the air to get in contact with the surface of the slurry.

As Comparative Example 6, a pre-treatment was exercised under the identical conditions as Example 2, but without adding any seed slurry.

As Comparative Example 7, the feed slurry was pre-treated under the identical conditions, but without stirring and adding seeds. As Comparative Example 8, the slurry was stored in a refrigerator at 2°-5° C., in lieu of subjecting it to the pre-treatment of Example 2.

Figure 3:
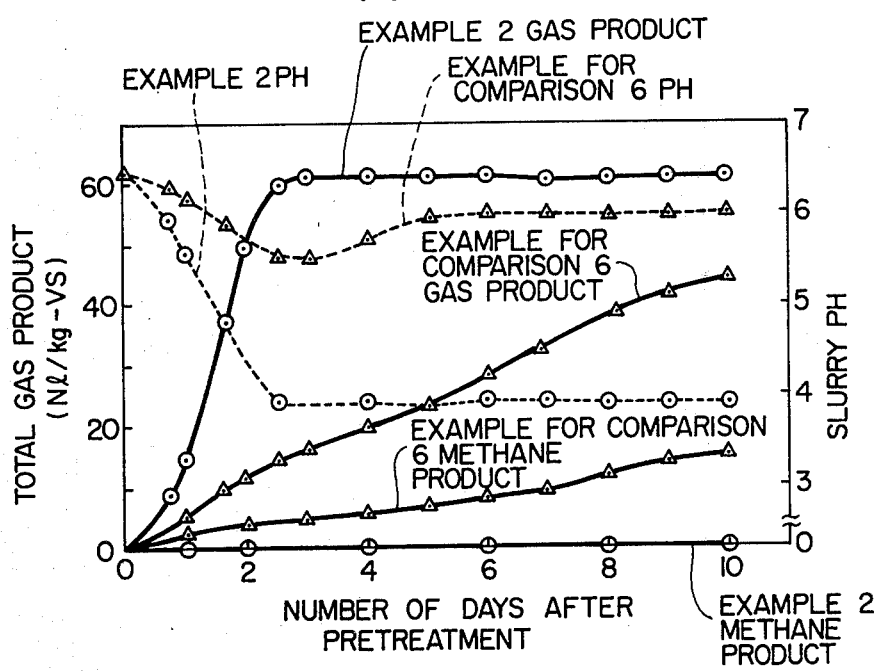
FIG. 3 exhibits the shifts in the amount of gas generated and the pH of the slurry in the course of operation in contrast with the corresponding values shown by the conventional process.

The results of measuring the gas product, methane product and the shift in pH respectively for Example 2 and Comparative Example 6 are shown in FIG. 3.

As it will be seen clearly from FIG. 3, in the case of Example 2 where the liquefying bacteria were added, it was observed that the partial liquefaction was completed within roughly 2 days, during which time the pH was acutely lowered. It was also known that after that stage there was little gas generation and possibly storable for at least 10 days with stability.

On the other hand, in the case of Comparative Example 6 where no liquefying bacterium was added, gasification fermentation also took place in parallel with liquefaction fermentation. For this reason, its pH remained within the range of 5-6, and never went down lower than that level. Since the optimum pH for gasification fermentation is 7-8, however, its gasification fermentation progressed slowly in a restrained manner, so that the methane gas of a lower purity which has a lesser utility value was being generated in this course.

The slurries subjected to partial liquefaction treatment for 1 day, 3 days and 10 days in Example 2 were respectively subjected to the main fermentation treatment by the liquefaction/gasification-mixed method. These three cases were designated as Examples 2-1, 2-2 and 2-3 respectively and their respective results are compiled in Table 3. The main fermentation by the liquefaction/gasification-mixed method was performed by charging the partially liquefied slurries into a 3 l fermenter with a stirrer, warm water jacket and an automatic pH adjuster for 12 days.

At the same time, the slurry partially liquefied for 3 days in Example 2 was also subjected to the main fermentation by the liquefaction/gasification-separated method, which was designated as Example 2-4, and its results are shown in Table 3. The main fermentation by the separated method was performed by charging continuously the partially liquefied slurry at the rate of 3 kg/day into a 0.75 l liquefaction treatment tank equipped with a stirrer, warm water jacket and an automatic pH adjuster for liquefaction treatment with a residential time of 3 days, and that was followed by a gasification treatment by way of charging continuously the liquefied slurry into a 2.25 l gasification tank having a stirrer and a warm water jacket with a residential time of 9 days.

Also, the respective slurries obtained by Comparative Example 5 through 8 were subjected to the main fermentation by a liquefaction/gasification-mixed method similar to Examples 2-1 through 2-3, and these cases were nominated as Comparative Examples 5-1, 6-1, 7-1 and 8-1 respectively, the respective results of which are also involved in Table 3.

TABLE 3

| | Items | | |
|---|---|---|---|
| | Daily Average* Total Gas Product (Nl/kg · VS) | Daily Average Methane Product (Nl/kg · VS) | Methane Purity (Volume %) |
| Example 2-1 | 630.5 | 364.0 | 58 |
| Example 2-2 | 575.3 | 373.8 | 65 |
| Example 2-3 | 573.3 | 364.0 | 63 |
| Example 2-4 | 669.5 | 383.5 | 78** |
| Comparative Example 5-1 | 345.8 | 162.5 | 47 |
| Comparative Example 6-1 | 617.5 | 341.3 | 55 |
| Comparative Example 7-1 | —*** | — | — |
| Comparative Example 8-1 | 718.3 | 364.0 | 51 |

Note:
*This does not include the gas product at the partial liquefaction step (pre-treatment), but only the gas product at the main fermentation.
**This indicates the methane concentration in the gas recovered from the gasification fermentation tank. No methane was detected in the gas recovered from the liquefaction tank.
***The gas exit pipe was blocked due to scum generation, and it was unable to operate.

As it is obviously observed from Table 3, the partial liquefaction treatment under an anaerobic condition with liquefying bacteria added facilitates efficient recovery of methane without any degradation which accompanies a loss of energy. In addition, the partial liquefaction makes it possible to upgrade the purity of the recovered methane gas. On the other hand, as indicated in Comparative Examples, either of a storing under a non-anaerobic condition and a storing without adding liquefying bacteria possess a drawback of lowering the recovered amount of methane gas.

EXAMPLE 3

50 kg of kitchen slurry (solid concentration 5%, organic concentration in the solids 84%) was prepared by crushing the home garbage which was kept at a room temperature for 1 day or 2 with a disposer after adding some water. The aforementioned kitchen slurry was fed into a 30 l fermenter made of acrylic plastics equipped with a stirrer and a warm water jacket, and 1 kg of liquefied slurry, which was separately prepared in advance through acclimation for an extended period of time, was added thereto.

The aforementioned slurry had been acclimated for about 1 month with a temperature set at 15° C. and pH at 6.2.

Next, the kitchen slurry to which the aforementioned slurry was added was subjected to a partial liquefaction treatment for 7 days under an anaerobic condition at 15° C. with no pH adjustment while kept stirred at 10 rpm (peripheral speed 7.5 m/min).

Further, as Comparative Example 9, a pre-treatment was performed on the kitchen slurry from the identical batch under the identical conditions as Example 3, but only without adding any liquefied slurry.

The shifts in the amount of gas generated as the time progresses in Example 3 and Comparative Example 9 respectively are shown in Table 3, and their pH, concentration of volatile fatty acid and the concentration of L-lactate are exhibited in Table 4.

TABLE 4

| | Items | | | | | |
|---|---|---|---|---|---|---|
| | pH | | Volatile Fatty Acid Concentration (Vol. %) | | L-Lactate Concentration (Vol. %) | |
| | Number of Days passed | | | | | |
| | 0 day | 3 days | 0 days | 3 days | 0 day | 3 days |
| Example 3 | 6.0 | 3.8 | 0.21 | 0.9 | 0.10 | 0.13 |
| Comparative Example 9 | 6.0 | 3.9 | 0.21 | 0.3 | 0.10 | 1.20 |

Figure 4:
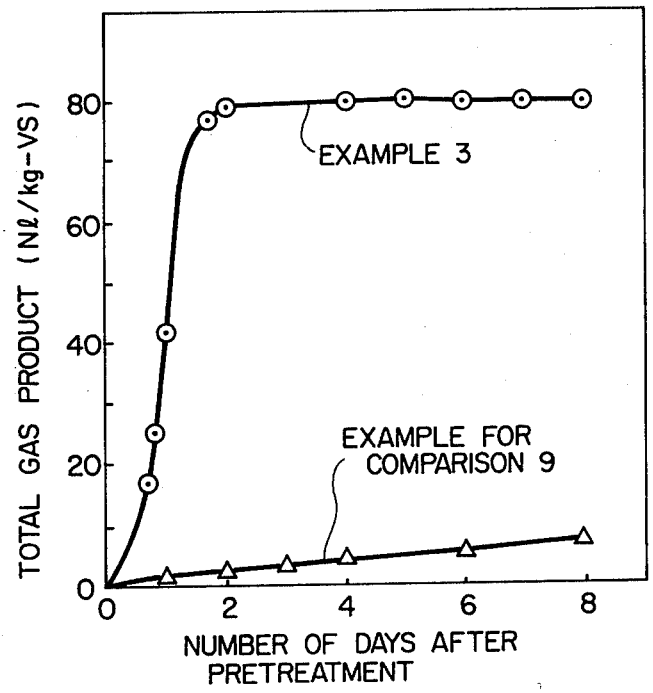
FIG. 4 shows the shift in the amount of gas generated in another example of the present invention in comparison with the values registered by the conventional process.

As it is seen in FIG. 4, in the case of Comparative Example 9 where no liquefied slurry was added, little generation of gas was observed. As shown in Table 4, however, pH went down to the range close to that of Example 3. This was due to the L-lactate which showed a marked increase while the generation of volatile fatty acid was kept rather small.

The slurries pre-treated in the cases of Example 3 and Comparative Examples were treated by the liquefaction/gasification-mixed method, by feeding respectively the above slurries continuously into a 3 l fermenter equipped with a stirrer, warm water jacket and an automatic pH adjuster at the rate of 0.3 kg slurry/day for fermentation with a residential time of 12 days. These cases, designated as Example 3-1 and Comparative Example 9-1 respectively, are shown in Table 5.

TABLE 5

|  | Daily Average* Total Gas Product (Nl/kg · VS) | Daily Average Methane Product (Nl/kg · VS) | Methane Purity (Vol. %) |
|---|---|---|---|
| Example 3-1 | 485.1 | 273.0 | 56 |
| Comparative Example 9-1 | 558.4 | 263.3 | 47 |

Note:
*This does not include the gas product at the partial liquefation step (pre-treatment), but only the gas product at the main fermentation.

Separately, the aforementioned pre-treated slurries were treated by a liquefaction/gasification-separated method. First, the pre-treated slurries respectively were fed continuously at the rate of 0.33 slurry/day into a 0.75 l liquefaction treatment tank equipped with a stirrer, warm water jacket and an automatic pH adjuster, and was treated with 2 residential time of 3 days. Next, the respective liquefied slurries were charged continuously into a 2.25 l gasification tank equipped with a stirrer and a warm water jacket, and was treated with a residential time of 9 days. The results of these two cases, identified as Example 3-2 and Comparative Example 9-2 respectively, are shown in Table 6.

TABLE 6

| | Items | | | |
|---|---|---|---|---|
| | Daily Average Gas Product at Liquefaction Tank (Nl/kg · VS) | Daily Average Gas Product at Gasification Tank (Nl/kg · VS) | Daily Average Methane Product (Nl/kg · VS) | Methane Purity (Vol. %) |
| Example 3-2 | 176.8 | 408.9 | 306.8 | 75 |
| Comparative Example 9-2 | 280.0 | 598.7 | 299.0 | 50 |

According to the results shown in Table 5, Example 3-1, in comparison with Comparative Example 9-1, excels in the methane purity, while it shows not much difference in the amount of methane recovered. On the other hand, according to the results as per Table 6, Comparative Example 9-2, as compared with Example 3-2, shows lesser gas generation at the liquefaction step whereas the gas product at the gasification step is increased that much. In the amount of gas produced, no significant difference is observed between two examples, similar to the cases shown in Table 5.

Therefore, the methane purity of the gas generated at the gasification tank is markedly higher in Example 3-2. Concluding the above detailed explanation together with some Examples on the process under the present invention, the process under the present invention facilitates to recover the amount of methane, comparable to the case of anaerobically digesting fresh organic wastes, but with much high purity, by anaerobically digesting the organic waste slurry as feedstock which has been partially liquefied and stored beforehand. Therefore, the process under the present invention possess a great utility value in industrial application.

What is claimed is:

1. An anaerobic digestion method for organic wastes consisting essentially of:
partially liquefying an organic waste slurry in the presence of liquefying bacteria of the facultative anaerobic bacteria group which are capable of converting organic materials to volatile fatty acid, while stirring without adjusting pH under an anaerobic condition to obtain a stable organic waste slurry; and
thereafter, liquefying and gasifying the treated slurry by adding to said slurry liquefying bacteria and gasifying bacteria of the obligatory anaerobic bacteria group which are capable of fermenting methane.

2. An anaerobic digestion method of organic wastes according to claim 1, wherein partial liquefaction is performed in a liquefaction tank and the amount of the aforementioned organic waste slurry to be partially liquefied can be varied, within the range of 20–100% (vol./Vol.) of the partial liquefaction tank's volume.

3. An anaerobic digestion method of organic waste slurry according to claim 2, wherein a partial liquefaction treatment is performed until the pH of the organic waste slurry becomes 2.0–4.5, in exercising a partial liquefaction treatment of such slurry.

4. An anaerobic digestion method of organic wastes according to claim 3, wherein, subsequent to the partial liquefaction treatment of the organic waste slurry, both of liquefaction fermentation and gasification fermentation are performed simultaneously within the same fermenter under the mixed presence of liquefying bacteria and gasifying bacteria.

5. An anaerobic digestion method of organic wastes according to claim 4, wherein the subsequent step where liquefying bacteria and gasifying bacteria are applied is performed at the temperature range identical to or proximate to that of the earlier step of partial liquefaction.

6. An anaerobic digestion method of organic wastes according to claim 1, wherein partial liquefaction treatment is performed until the pH of the organic waste slurry becomes 2.0–4.5, in exercising a partial liquefaction treatment of such slurry.

7. An anaerobic digestion method of organic wastes according to claim 6, wherein, subsequent to the partial liquefaction treatment of the organic waste slurry, both liquefaction fermentation and gasification fermentation are performed simultaneously within the same fermenter under the mixed presence of liquefying bacteria and gasifying bacteria.

8. An anaerobic digestion method of organic wastes according to claim 7, wherein the subsequent step where liquefying bacteria and gasification bacteria are applied is performed at the temperature range identical to or proximate to that of the earlier step of partial liquefaction.

9. An anaerobic digestion method of organic wastes according to claim 7, wherein the partial liquefaction treatment of the organic waste slurry is performed within the temperature range lower than that for the subsequent treatment step which applies liquefying bacteria and gasifying bacteria.

10. An anaerobic digestion method of organic wastes according to claim 1, wherein the partial liquefaction treatment of the organic waste slurry is performed within a temperature range lower than that for the subsequent treatment step which applies liquefying bacteria and gasification bacteria.

11. An anaerobic digestion method according to claim 1, wherein partial liquefaction progressed until the concentration of volatile fatty acid in the slurry reaches 4,000–15,000 ppm.

12. A method for the anaerobic digestion of organic wastes comprising the steps of:
(a) partially liquefying and storing an organic waste slurry under anaerobic conditions in the presence of liquefying bacteria of the facultative anaerobic bacteria group which are capable of converting organic materials to volatile fatty acids, while stirring and without adjusting the pH of the slurry thereby preventing the generation of methane and thereby obtaining a stable acidic organic waste slurry; and
(b) thereafter, at a higher pH, liquefying and gasifying the treated slurry by adding to said slurry liquefying bacteria and gasifying bacteria of the obligatory anaerobic bacteria groups which are capable of fermenting methane.

13. An anaerobic digestion method of organic wastes according to claim 12, wherein the partial liquefaction step and the subsequent simultaneous liquefaction/gasification step are performed with the liquefying bacteria of the same strain, and wherein a part of the treated slurry at the simultaneous liquefaction/gasification step is recycled back to the earlier step for partial liquefaction.

14. An anaerobic digestion method according to claim 1 or 12, wherein the partial liquefaction is performed at a temperature of 10°–45° C.

15. An anaerobic digestion method according to claim 1 or 12, wherein the partial liquefaction is performed at a temperature of 10° to 30° C.

16. An anaerobic digestion method for organic wastes comprising the steps of:
partially liquefying an organic waste slurry at a temperature of from 10° to 30° C. in the presence of liquefying bacteria of the facultative anaerobic bacteria group which are capable of converting organic materials to volatile fatty acid, while stirring without adjusting pH under an anaerobic condition to obtain a stable organic waste slurry, said partial liquefaction treatment being performed until the pH of said organic waste slurry is from 2.0 to 4.5; and
thereafter, at a higher pH, liquefying and gasifying the treated slurry by adding to said slurry liquefying bacteria and gasifying bacteria of the obligatory anaerobic bacteria group which are capable of fermenting methane.

17. An anaerobic digestion method of organic wastes according to claim 16, wherein partial liquefaction is performed in a liquefaction tank and the amount of the aforementioned organic waste slurry to be partially liquefied can be varied, within the range of 20–100% (vol./Vol.) of the partial liquefaction tank's volume.

18. An anaerobic digestion method for organic wastes according to claim 16, wherein, subsequent to the partial liquefaction treatment of the organic waste slurry, both liquefaction, fermentation and gasification fermentation are performed simultaneously within the same fermenter under the mixed presence of liquefying bacteria and gasifying bacteria, and wherein a portion of the treated slurry obtained from the simultaneous liquefaction/gasification step is recycled back to the partial liquefaction step.

* * * * *